United States Patent [19]

Naskar et al.

[11] 4,366,100

[45] Dec. 28, 1982

[54] BIODEGRADABLE, OXIDATION-RESISTANT LIQUID ESTER MIXTURES WITH LOW TURBIDITY POINTS

[75] Inventors: Sasanka S. Naskar; Reinhard Pass, both of Witten, Fed. Rep. of Germany

[73] Assignee: Dynamit Nobel AG, Troisdorf, Fed. Rep. of Germany

[21] Appl. No.: 280,028

[22] Filed: Jul. 2, 1981

Related U.S. Application Data

[63] Continuation of Ser. No. 117,723, Feb. 1, 1980, abandoned.

[30] Foreign Application Priority Data

Feb. 3, 1979 [DE] Fed. Rep. of Germany ....... 2904164
Sep. 29, 1979 [DE] Fed. Rep. of Germany ....... 2939663

[51] Int. Cl.$^3$ ................................................ C11C 3/02
[52] U.S. Cl. ............................... 260/410.7; 260/410.8; 560/199
[58] Field of Search .......................... 260/410.7, 410.8; 560/199

[56] References Cited

U.S. PATENT DOCUMENTS

| | | | |
|---|---|---|---|
| Re. 25,696 | 12/1964 | Houben et al. | 260/410.8 |
| 3,000,917 | 9/1961 | Babayan | 560/199 |
| 3,766,227 | 10/1973 | Banger | 260/410.8 |
| 4,089,874 | 5/1978 | Naskar et al. | 260/410.7 |
| 4,234,498 | 11/1980 | Lok | 260/410.7 |

*Primary Examiner*—Thomas A. Waltz
*Attorney, Agent, or Firm*—Sprung, Horn, Kramer & Woods

[57] ABSTRACT

Completely biodegradable, toxicologically innocuous, oxidation-resistant, flavorless and odorless, light-colored, homogeneous liquid ester mixtures with low turbidity points, low evaporation losses at elevated temperatures, and viscosities and densities adjustable as desired, comprising the products of esterification of 1 mol of glycerin with from 1.4 to 2.8 mols of a saturated aliphatic monocarboxylic acid having from 6 to 10 carbon atoms, or mixtures thereof, and from 0.1 to 0.8 mol of a saturated aliphatic dicarboxylic acid, or mixtures or anhydrides thereof, said ester mixtures having hydroxyl numbers ranging from 5 to 20 and an acid number of less than 5.

11 Claims, No Drawings

BIODEGRADABLE, OXIDATION-RESISTANT LIQUID ESTER MIXTURES WITH LOW TURBIDITY POINTS

This is a continuation, of application Ser. No. 117,723, filed Feb. 1, 1980, now abandoned.

The invention relates to completely biodegradable, toxicologically innocuous, oxidation-resistant, flavorless and odorless, light-colored, homogeneous liquid ester mixtures having low turbidity points, low evaporation losses at elevated temperatures, and viscosities and densities adjustable as desired, which consist of the products of esterification of 1 mol glycerin with from 1.4 to 2.8 mols, and preferably 1.6 to 2.6 mols, of a saturated aliphatic monocarboxylic acid having from 6 to 10 carbon atoms, or mixtures thereof, and from 0.1 to 0.8 mol, and preferably 0.2 to 0.7 mol, of an unsaturated aliphatic dicarboxylic acid. The new ester mixtures have hydroxyl numbers ranging from 5 to 20 and an acid number of less than 5.

The object of the invention is the preparation of homogeneous liquid ester mixtures whose physical properties are superior, with respect to solidification point and turbidity point as well as oxidation resistance, to those of naturally occurring oils, and whose viscosity and density can be adjusted as required by the end use, from industrially available raw materials by a simple, economical process. More particularly, the invention relates to component systems which are completely biodegradable and therefore ecologically innocuous. The ester mixtures prepared in accordance with the invention find special uses in the field of cosmetics and in the technical sector in metal forming, glass-fiber treatment, as lubricant additives, etc.

Because they are completely biodegradable, naturally occurring oils which at ambient temperature are liquid do lend themselves to use in the field of cosmetics and in the technical sector. However, the requirements of the various industries with regard to high quality and specific properties for particular end uses vary so widely that a naturally occurring oil cannot always meet them.

The turbidity point, or low-temperature stability, of natural oils does not extend much below 8° C. The viscosities and densities have narrow limits. The viscosity at 20° C., for example, ranges from 50 to 90 mPs (millipascals) (except in the case of castor oil, where it is about 1000 mPs), and the density at 25° C. is about 0.9.

Another undesirable property of natural oils is their low stability to oxidation, which accounts for their tendency to gum and to exude corrosive fatty acids. This behavior is due to their content of unsaturated fatty acids.

Efforts to remedy some of these disadvantages, and particularly the lack of oxidation resistance, have led to triglycerides of midchain-saturated fatty acids, which are flavorless, odorless, oxidation-resistant, biodegradable liquid ester mixtures. The viscosity of such products, such as Miglyol 812 ® of Dynamit Nobel AG, at 20° C. is about 30 mPs, and the turbidity point is rarely below −5° C.

The drawbacks of natural oils can be overcome by the use of paraffin oils. Refined paraffin oils, known as white oils and forming clear, colorless liquids of oily character, are mixtures of saturated hydrocarbons of varying viscosities and with low turbidity points. They are stable to oxidation and have broad uses in the cosmetics and technical sectors. Major disadvantages, however, are their low biodegradability and high evaporation losses at elevated temperatures.

The inventors thus have sought to develop a process for the economical production of a completely biodegradable, oxidation-resistant, homogeneous liquid ester mixture with low solidification and turbidity points and good viscosity indices which has relatively low evaporation losses at elevated temperatures and which because of its particular physical properties lends itself to use especially in the cosmetics and technical sectors, said process using also aliphatic dicarboxylic acids other than succinic acid or its anhydride.

SUMMARY OF THE INVENTION

Broadly, this invention contemplates a completely biodegradable, toxicologically innocuous, oxidation resistant, flavorless and odorless, light-colored, homogeneous liquid ester mixture of low turbidity point, low evaporation losses at elevated temperature and adjustable viscosity and density comprising the product of esterification of 1 mol glycerin with 1.4 to 2.8 mols of a saturated aliphatic monocarboxylic acid having from 6 to 10 carbon atoms, or mixtures thereof, and from 0.1 to 0.8 mol of saturated aliphatic dicarboxylic acid or mixtures or anhydrides thereof, said ester or mixture of esters having a hydroxyl number from 5 to 20 and an acid number of less than 5. The sum of the acid radicals is always 3 mols per mol of glycerin so that the products are practically free of hydroxyl groups. Surprisingly, with increased aliphatic dicarboxylic acid contents of from 0.1 to 0.8 mol and correspondingly decreasing saturated aliphatic monocarboxylic acid contents of from 2.8 to 1.4 mols, esterification products having very low turbidity points but rising viscosity indices are obtained. As the content of aliphatic dicarboxylic acids increases, the turbidity points drop to very low temperatures, and the viscosity rises correspondingly to very high levels. Such ester mixtures are completely biodegradable, oxidation-resistant, flavorless and odorless, light-colored, homogeneous and liquid and have low solidification and turbidity points, low evaporation losses at elevated temperatures, and good viscosity indices and densities which can be adjusted as desired.

By aliphatic dicarboxylic acids are meant the saturated dicarboxylic acids, and particularly those having from 4 to 10 carbon atoms. Especially well suited are the α,ω-dicarboxylic acids; however, branched-chain dicarboxylic acids such as methylglutaric acid should not be ruled out altogether. Preferred acids are succinic, glutaric, adipic, sebacic and azelaic acids. Mixtures of these dicarboxylic acids and, optionally, their anhydrides are also suitable.

By saturated monocarboxylic acids, the straight-chain fatty acids are meant, especially the alkanoic acids.

The disadvantages of naturally occurring oils, such as unpleasant odor, low stability to oxidation, higher turbidity points, and low viscosity and density, and the poor biodegradability of paraffin oils and their high evaporation losses at elevated temperatures, thus are not encountered with the substances in accordance with the invention. Depending on the particular contents of dicarboxylic acid esters in the esterification product, the products generally have turbidity points ranging from −10° to −70° C., viscosities from 50 to 5000 mPs, densities between 0.96 and 1.07, and evaporation losses ranging from 14 to 32% during 100 hours at 150° C. and normal pressure.

A further object of the invention is a process for the preparation of such ester mixtures by the esterification of glycerin with a saturated aliphatic monocarboxylic acid having from 6 to 10 carbon atoms, or mixtures thereof, in the ratio of 1 mol of glycerin to from 1.4 to 2.8 mols, and preferably 1.8 to 2.6 mols, of saturated aliphatic monocarboxylic acid, at from 200° to 250° C., preferably under vacuum, to hydroxyl-containing partial esters until an acid number of less than 50, and preferably less than 10, is obtained, and, concurrently with their formation or following it, the further esterification of the hydroxyl-containing partial esters with from 0.1 to 0.8 mol, and preferably from 0.2 to 0.7 mol, of aliphatic dicarboxylic acids, or their mixtures or anhydrides, at from 200° to 250° C., preferably under vacuum, until a hydroxyl number of from 5 to 20 and an acid number of less than 5, and preferably less than 1, is obtained, followed by conventional decolorization and deodorization of the crude product.

Preferably, glycerin is esterified with a saturated aliphatic monocarboxylic acid having 6 to 10 carbon atoms, or mixtures thereof, and simultaneously with aliphatic dicarboxylic acids or mixtures or anhydrides thereof, at from 200°–250° C., preferably 220°–240° C., under a vacuum until a hydroxyl number ranging from 5 to 20 and acid number less than 5, preferably less than 1, are obtained.

The hydroxyl containing glycerin partial esters can be prepared in the absence of the aliphatic dicarboxylic acids, anhydrides or mixtures, preferably at 200°–250° C. and thereafter esterified with such aliphatic dicarboxylic acids.

When the preparation is performed under a vacuum, the vacuum is gradually increased by about 5 to 50 mm Hg, preferably 10 to 20 mm Hg, per hour in the presence of the aliphatic dicarboxylic acid or mixtures or anhydrides.

With molar ratios of glycerin to dicarboxylic acid under 1:0.6, all reactants can be esterified at the same time. With higher molar ratios, the dicarboxylic acids are added only after the fatty acid partial esters have been cooled to 140° C. With both methods, whether the aliphatic dicarboxylic acids are added simultaneously or subsequently, the esterification must be carried out under vacuum when the acid number during esterification at from 220° to 240° C. is less than 60. Once the vacuum has reached 350 mm Hg, it is improved by from 5 to 50 mm Hg per hour until the acid number drops below 5, and preferably below 1. Here the use of a dephlegmator is indicated.

The products are physiologically innocuous.

The first-fraction coconut fatty acid used in the preparation of the esterification products is a distillate fraction with about 1% $C_6$, 58% $C_8$ and 41% $C_{10}$ acid obtained in the distillation of coconut fatty acid. The pure $C_6$ to $C_{10}$ fatty acids might also be used, but they offer no particular advantages over fatty acid mixtures so far as their properties are concerned. Natural heptanoic acid is also available commercially (from ATO-Chemie, for example).

The esterification products based on glycerin, saturated aliphatic monocarboxylic acid mixtures with from 6 to 10 carbon atoms, or heptanoic acid and aliphatic dicarboxylic acids or mixtures thereof are characterized by the following special advantages:

1. They are odorless, flavorless and light-colored homogeneous liquids with low turbidity points which range from −16° to −70° C. The turbidity points of natural oils are much higher. That of peanut oil, for example, is about 8° C. Miglyol 812 ®, a triglyceride of $C_8$ to $C_{10}$ fatty acids, has a turbidity point of −5° C.
2. They exhibit excellent stability to atmospheric air during storage because of the absence of unsaturated compounds. By contrast, all natural oils contain unsaturated fatty acids which give rise to rancidity and unpleasant odor during storage.
3. The viscosity and density can be adjusted as desired by means of the aliphatic dicarboxylic acid content of the esterification products. The viscosity of natural oils ranges from 60 to 90 mPs at 20° C. while the density is about 0.9 at 25° C. The viscosity of the products of the invention, on the other hand, ranges from about 50 to 3200 mm$^2$/sec, and the density from about 0.966 to 1.078 at 20° C.
4. The evaporation losses at elevated temperatures are reduced by the incorporation of dicarboxylic acid in the esterification products. Miglyol 812 ® shows a loss of 42.9% during 100 hours at 150° C. With increasing amounts of aliphatic dicarboxylic acids, the volatilities are markedly reduced. Even a paraffin oil of comparable viscosity exhibits a decidedly higher evaporation loss. Viscous paraffin oil (202 mm$^2$/sec), for example, has a loss of 39.3% while an adipic acid-esterified $C_6$ to $C_{10}$ glycerin partial ester of the same viscosity has a loss of only 21.8%.
5. Like natural oils, the esterification products are completely biodegradable whereas the paraffin oils are only difficultly biodegradable, if at all.
6. By comparison with conventional mineral oil products and naturally occurring oils of the same viscosity, the ester mixtures in accordance with the invention have lower solidification points and very good viscosity indices. The viscosities of such ester mixtures at 40° C. range from about 20 to 1000 mPs, and more particularly from 30 to 150 mPs, and at 100° C. from 5 to 100 mPs, and more particularly from 10 to 30 mPs. The solidification points are under −30° C.

The examples which follow will serve to illustrate the invention without, however, limiting it.

EXAMPLE 1

In a 2-liter three-neck flask equipped with agitator, water separator, dephlegmator, thermometer and gas inlet pipe, a mixture of 276 g (3 mols) glycerin, 88 g (0.6 mol) adipic acid and 1209 g (7.8 mols) first-fraction coconut fatty acid (a $C_6$ to $C_{10}$ fatty acid mixture) was esterified for 2 hours at 240° C. and 350 mm Hg in the presence of 0.5 g isopropyl titanate with agitation and simultaneous introduction of an inert gas, and the reaction water was eliminated until an acid number of 60 was obtained. Esterification was then continued at a reaction temperature of 240° C. while the vacuum was being increased stepwise (50 mm Hg/hour) until an acid number of less than 2 was obtained, the reaction water and the intermediate product formed being separated, by means of a diphlegmator heated to from 100° to 120° C., in such a way that only the reaction water needed to be eliminated. With decreasing acid number, the intermediate product was completely converted in the process. The crude ester obtained was deodorized for 2 hours at 170° C. and 10 mm Hg, following which it was bleached for 0.5 hour at 120° C. with 10 g of fuller's earth and then pressure-filtered with 5 g of filter aid.

Acid number: 0.4
Hydroxyl number: 8.0
Viscosities: 20° C.—54.9 mm$^2$/sec, 37.8° C.—23.6 mm$^2$/sec, 98.8° C.—5.0 mm$^2$/sec
Density: 0.966 at 20° C.
Turbidity point: −22° C.
Evaporation loss during 100 h at 100° C.: 31.3%
Solidification point: −26° C.
Viscosity index: 144

EXAMPLE 2

In the reaction apparatus described in Example 1, a mixture of 322 g (3.5 mols) glycerin, 205 g (1.4 mols) adipic acid and 1209 g (7.8 mols) first-fraction coconut fatty acid was esterified for 3 hours at 240° C. and 350 mm Hg in the presence of 0.5 g butyl titanate as catalyst under an inert gas to an acid number of 40. Esterification was then continued at 240° C. with stepwise improvement of the vacuum (50 mm Hg/hour) and elimination of the residual reaction water in the manner described in Example 1 until an acid number of less than 1 was obtained. The crude ester was deodorized, bleached and filtered as in Example 1.

Acid number: 0.8
Hydroxyl number: 11.5
Density: 0.987 at 20° C.
Viscosities: 20° C.—119 mm$^2$/sec, 37.8° C.—45.8 mm$^2$/sec, 98.8° C.—8.1 mm$^2$/sec
Turbidity point: −38° C.
Evaporation loss during 100 h at 100° C.: 23.4%
Solidification point: −44° C.
Viscosity index: 149

EXAMPLE 3

In a 10-liter three-neck flask equipped with agitator, water separator, dephlegmator, thermometer and inert-gas inlet pipe, a mixture of 1630 g (17.7 mols) glycerin, 1374 g (9.4 mols) adipic acid and 5317 g (34.3 mols) first-fraction coconut fatty acid was esterified at 240° C. and 350 mm Hg in the presence of 3 g butyl titanate under an inert gas until an acid number of 65 was obtained. Over a period of 6 hours at 240° C., the vacuum was improved by about 50 mm Hg/hour. The reaction water formed was separated from the intermediate product by means of a dephlegmator heated to 100° to 120° C. and further esterified until an acid number of less than 1 was obtained.

The crude ester was then deodorized for 4 hours at 170° C. and 10 mm Hg, bleached for 1 hour with 40 g fuller's earth, and pressure-filtered with 20 g filter aid.

Acid number: 0.6
Hydroxyl number: 9.2
Density: 1.007 at 20° C.
Viscosities: 20° C.—228 mm$^2$/sec, 37.8° C.—78.0 mm$^2$/sec, 98.8° C.—12.5 mm$^2$/sec
Turbidity point: −55° C.
Evaporation loss during 100 h at 100° C.: 22.3%
Solidification point: −48° C.
Viscosity index: 150

EXAMPLE 4

By the procedure of Example 3, 1501 g (16.3 mols) glycerin, 1432 g (9.8 mols) adipic acid and 4542 g (29.3 mols) first-fraction coconut fatty acid were esterified in the presence of 3 g 2-ethylhexyl titanate until an acid number of less than 2 was obtained, deodorized, bleached and filtered.

Acid number: 0.6
Hydroxyl number: 12.9
Density: 1.020 at 20° C.
Viscosities: 20° C.—358 mm$^2$/sec, 37.8° C.—119 mm$^2$/sec, 98.8° C.—16.7 mm$^2$/sec
Turbidity point: −64° C.
Evaporation loss during 100 h at 100° C.: 20.6%
Solidification point: −41° C.
Viscosity index: 151

EXAMPLE 5

In a 2-liter three-neck flask equipped with agitator, water separator, thermometer and inert-gas inlet pipe, a mixture of 396 g (4.3 mols) glycerin and 930 g (6 mols) first-fraction coconut fatty acid was heated to 240° C. at 350 mm Hg in the presence of 0.5 g isopropyl titanate with agitation and simultaneous introduction of inert gas, and the reaction water was eliminated until an acid number of less than 10 was obtained. The partial ester obtained was cooled to 140° C. After the addition of 504 g (3.45 mols) adipic acid, the temperature was raised to 240° C. with agitation and under an inert gas, and the reaction water formed was separated by means of a dephlegmator heated to 100° to 120° C. in such a way that only the reaction water was eliminated and the vacuum was improved to 5 mm Hg. After an acid number of less than 1 had been obtained, the crude ester was cooled and deodorized, bleached and filtered in the usual manner.

Acid number: 0.7
Hydroxyl number: 16.5
Density: 1.050 at 20° C.
Viscosities: 20° C.—2410 mm$^2$/sec, 37.8° C.—670 mm$^2$/sec, 98.8° C.—68.3 mm$^2$/sec
Turbidity point: Under −70° C.
Evaporation loss during 100 h at 100° C.: 16.9%
Solidification point: −27° C.
Viscosity index: 177

EXAMPLE 6

By the procedure of Example 1, 276 g (3 mols) glycerin, 88 g (0.6 mol) adipic acid and 1016 g (7.8 mols) heptanoic acid were esterified.

Acid number: 0.6
Hydroxyl number: 17.8
Density: 0.992 at 20° C.
Viscosities: 20° C.—39.2 mm$^2$/sec, 37.8° C.—18.0 mm$^2$/sec, 98.8° C.—4.2 mm$^2$/sec
Turbidity point: Under −70° C.
Solidification point: −66° C.
Viscosity index: 141

EXAMPLE 7

By the procedure of Example 2, 322 g (3.5 mols) glycerin, 205 g (1.4 mols) adipic acid and 1016 g (7.8 mols) heptanoic acid were esterified.

Acid number: 0.6
Hydroxyl number: 15.7
Density: 1.016 at 20° C.
Viscosities: 20° C.—90.1 mm$^2$/sec, 37.8° C.—38.9 mm$^2$/sec, 98.8° C.—7.1 mm$^2$/sec
Turbidity point: Under −70° C.
Solidification point: −55° C.
Viscosity index: 147

EXAMPLE 8

By the procedure of Example 3, 1501 g (16.3 mols) glycerin, 1432 g (9.8 mols) adipic acid and 3815 g (29.3 mols) heptanoic acid were esterified.
Acid number: 0.8
Hydroxyl number: 4.3
Density: 1.041 at 20° C.
Viscosities: 20° C.—304 mm$^2$/sec, 37.8° C.—114 mm$^2$/sec, 98.8° C.—16.2 mm$^2$/sec
Turbidity point: Under −70° C.
Solidification point: −44° C.
Viscosity index: 157

EXAMPLE 9

By the procedure of Example 5, 396 g (4.3 mols) glycerin, 781 g (6 mols) heptanoic acid and 504 g (3.45 mols) adipic acid were esterified.
Acid number: 0.4
Hydroxyl number: 14.3
Density: 1.078 at 20° C.
Viscosities: 20° C.—3175 mm$^2$/sec, 37.8° C.—976 mm$^2$/sec, 98.8° C.—89.0 mm$^2$/sec
Turbidity point: Under −70° C.
Solidification point: −30° C.
Viscosity index: 177

EXAMPLE 10

By the procedure of Example 1, 276 g (3 mols) glycerin, 121 g (0.6 mol) sebacic acid and 1209 g (7.8 mols) first-fraction coconut fatty acid were esterified.
Acid number: 0.4
Hydroxyl number: 5.8
Density: 0.962 at 20° C.
Viscosities: 20° C.—60.6 mm$^2$/sec, 37.8° C.—26.2 mm$^2$/sec, 98.8° C.—5.5 mm$^2$/sec
Turbidity point: −18° C.
Evaporation loss during 100 h at 100° C.: 32.2%
Solidification point: −16° C.
Viscosity index: 154

EXAMPLE 11

By the procedure of Example 2, 322 g (3.5 mols) glycerin, 283 g (1.4 mols) sebacic acid and 1209 g (7.8 mols) first-fraction coconut fatty acid were esterified.
Acid number: 1.0
Hydroxyl number: 0.8
Density: 0.978 at 20° C.
Viscosities: 20° C.—129 mm$^2$/sec, 37.8° C.—49.7 mm$^2$/sec, 98.8° C.—9.0 mm$^2$/sec
Turbidity point: −33° C.
Evaporation loss during 100 h at 100° C.: 26%
Solidification point: −35° C.
Viscosity index: 164

EXAMPLE 12

By the procedure of Example 4, 1501 g (16.3 mols) glycerin, 1982 g (9.8 mols) sebacic acid and 4542 g (29.3 mols) first-fraction coconut fatty acid were esterified.
Acid number: 0.4
Hydroxyl number: 13.8
Density: 0.996 at 20° C.
Viscosities: 20° C.—483 mm$^2$/sec, 37.8° C.—166 mm$^2$/sec, 98.8° C.—23.1 mm$^2$/sec
Turbidity point: −34° C.
Evaporation loss during 100 h at 100° C.: 21.4%
Solidification point: −36° C.
Viscosity index: 168

EXAMPLE 13

By the procedure of Example 2, 276 g (3.0 mols) glycerin, 311 g (1.65 mols) azelaic acid and 884 g (5.7 mols) first-fraction coconut fatty acid were esterified.
Acid number: 0.4
Hydroxyl number: 6.5
Density: 0.999 at 20° C.
Viscosities: 20° C.—319 mm$^2$/sec, 37.8° C.—112 mm$^2$/sec, 98.8° C.—16.5 mm$^2$/sec
Turbidity point: −46° C.
Evaporation loss during 100 h at 100° C.: 18.1%
Solidification point: −42° C.
Viscosity index: 162

EXAMPLE 14

By the procedure of Example 2, 322 g (3.5 mols) glycerin, 40 g (0.35 mol) glutaric acid and 1322 g (10.15 mols) heptanoic acid were esterified.
Acid number: 0.18
Hydroxyl number: 16.7
Density: 0.984 at 20° C.
Viscosity: 20° C.—38.5 mm$^2$/sec
Turbidity point: Under −70° C.
Solidification point: −66° C.

EXAMPLE 15

In a 2-liter three-neck flask equipped with agitator, water separator, dephlegmator, thermometer and gas inlet pipe, a mixture of 276.3 g (3 mols) glycerin, 60 g (0.6 mol) succinic anhydride and 1202 g (7.8 mols) first-fraction coconut fatty acid (a $C_6$ to $C_{10}$ fatty acid mixture) was heated to and maintained at 240° C. and 350 mm Hg for 2 hours in the presence of 0.5 g isopropyl titanate with agitation and simultaneous introduction of an inert gas, and the reaction water was eliminated until an acid number of 60 was obtained. Esterification was then continued at a reaction temperature of 240° C. while the vacuum was being increased stepwise (50 mm Hg/hour) until the acid number dropped below 2, the reaction water and the intermediate product formed being separated by means of a dephlegmator heated to 100° to 120° C. in such a way that only the reaction water was eliminated. With decreasing acid number, the intermediate product was converted completely. The crude ester obtained was deodorized for 2 hours at 170° C. and 10 mm/Hg and with the addition of 10 g fuller's earth and 5 g filter aid bleached at 120° C. and then pressure-filtered.

Acid number, 0.2; Hazen color index, 50; density, 0.966 at 20° C.; viscosity at 20° C., 52.4 mPs; turbidity point, −16° C.; evaporation loss during 100 h at 100° C., 31.3%.

EXAMPLE 16

In the reaction apparatus described in Example 15, a mixture of 322 g (3.5 mols) glycerin, 140 g (1.4 mols) succinic anhydride and 1186 g (7.8 mols) first-fraction coconut fatty acid (a $C_6$ to $C_{10}$ fatty acid mixture) was esterified for 3 hours at 240° C. and 350 mm Hg under an inert gas in the presence of 0.5 g butyl titanate as catalyst until an acid number of 40 was obtained. Esterification was then continued at 240° C. while the vacuum was being improved stepwise (50 mm Hg/hour) and the residual reaction water was being eliminated, in the manner described in Example 15, until an acid number of less than 1 was obtained. The crude ester obtained was deodorized, bleached and filtered as in Example 15.

Acid number, 0.2; saponification number, 393; hydroxyl number, 8.6; Hazen color index, 50; density, 0.992 at 20° C.; viscosity at 20° C., 116.8 mPs; turbidity point, −37° C.; evaporation loss during 100 hours at 100° C., 24.9%.

EXAMPLE 17

In a 10-liter three-neck flask equipped with agitator, water separator, dephlegmator, thermometer and inert-gas inlet pipe, a mixture of 1628 g (17.7 mols) glycerin, 972 g (9.7 mols) succinic anhydride and 5173 g (33.6 mols) first-fraction fatty acid (a $C_6$ to $C_{10}$ fatty acid mixture) was esterified in the presence of 3 g butyl titanate under an inert gas at 240° C. and 350 mm Hg until an acid number of 65 was obtained. Over a period of 6 hours the vacuum was improved by about 50 mm Hg/hour at 240° C. The reaction water formed was separated from the intermediate product by means of a dephlegmator heated to 100° to 120° C. and esterification was continued until the acid number dropped below 1.

The crude ester was deodorized for 4 hours at 170° C. and 10 mm Hg, bleached for 1 hour at 120° C. with the addition of 40 g fuller's earth and 20 g filter aid, and pressure-filtered.

Acid number, 0.6; saponification number, 418; hydroxyl number, 9.2; Hazen color index, 60; density, 1.012 at 20° C.; viscosity at 20° C., 257 mPs; turbidity point, −51° C.; evaporation loss during 100 h at 100° C., 20.3%.

EXAMPLE 18

By the procedure of Example 17, 1503 g (16.3 mols) glycerin, 980 g (9.8 mols) succinic anhydride and 4523 g (29.4 mols) first-fraction coconut fatty acid were esterified in the presence of 3 g ethylhexyl titanate until an acid number of less than 2 was obtained, followed by deodorization, bleaching and filtering.

Acid number, 1.0; saponification number, 433; hydroxyl number, 7.5; Hazen color index, 60; density, 1.026 at 20° C., viscosity at 20° C., 382 mPs; turbidity point, under −30° C.; evaporation loss during 100 h at 100° C., 19.4%.

EXAMPLE 19

In a 2-liter three-neck flask equipped with agitator, dephlegmator, water separator, thermometer and inert-gas inlet pipe, a mixture of 396 g (4.3 mols) glycerin and 928 g (6 mols) first-fraction coconut fatty acid was heated in the presence of 0.5 g isopropyl titanate to 240° C. at 350 mm Hg with agitation and simultaneous introduction of inert gas and the reaction water was eliminated until an acid number of less than 10 was obtained. The partial ester obtained was cooled to 140° C. After the addition of 345 g (3.45 mols) succinic anhydride, the temperature was raised to 240° C. with agitation and under inert gas, and the reaction water formed was separated by means of a dephlegmator heated to 100° to 120° C. in such a way that only the reaction water was eliminated and the vacuum was improved stepwise to 5 mm Hg. After an acid number of less than 1 had been obtained, the crude ester was cooled and deodorized, bleached and filtered in the usual manner.

Acid number, 0.24; saponification number, 478; hydroxyl number, 13.6; Hazen color index, 70; density, 1.069 at 20° C.; viscosity at 20° C., 4463 mPs; turbidity point, under −70° C.; evaporation loss, 14.1%.

Table 1 which follows describes the developed products obtained in the examples in greater detail and compares them with naturally occurring oils, such as peanut oil and a commercial paraffin oil of medium viscosity.

EXAMPLE 20:(USE)

Preparation of a gel-like adsorption base and its use as a cream basis

Composition of the Emulsion:

35 weight-parts of adsorption base (oil base)
65 weight-parts of aqueous phase (62,5 wt.-parts water
0,3 wt.-parts MgSO$_4$
0,2 wt.-parts p-hydroxy-benzoic acid propyl ester
2,0 wt.-parts sorbitol)

Composition and Preparation of the Adsorption Base (oil base)

40 wt.-parts paraffin oil 35 wt.-parts of the esterification products prepared in Examples 1 to 19

7 wt.-parts BENTONE 27 R (Titangesellschaft, Leverkusen)

3 wt.-parts propylene glycol 25 wt.-parts of Pentaerythritolmonooleat as emulsifier.

The components of the adsorption base are vigorously stirred at 120° C. for one hour. After this mixture has cooled down to 80° C., 35 wt.-parts of the gel-like adsorption base is diluted with 65 wt.-parts of aqueous phase having an 80° C. temperature, with constant stirring.

Stirring is continued until the mass has cooled, and a smooth cream is obtained.

According to stability tests of the so formed emulsions a remarable good storage stability of 6 month at 25° C., three month at 40° C. and two weeks at 55° C. and a good thaw-freeze stability during test cycles of freeze at −15° C. for 16 hours and then thaw at 20° C. for 8 hours of at least 8 cycles was found for all emulsions, being a very fine stability of creams based on water containing emulsions.

TABLE 1

| Example | Composition Substances | Mols S per mol G | Acid number | Sapon. number | Hydroxyl number | Turbidity point °C. | Evaporation loss 150° C./100 h | Viscosity (mm$^2$/sec) | Density (20° C.) |
|---|---|---|---|---|---|---|---|---|---|
| Miglyol ® | * | | 0.1 | 340 | 5.1 | 5 | 42.9% | 29.8 | 0.950 |
| Peanut oil | ** | | 0.11 | 188 | 3.8 | 8 | 6.8% | 93.6 | 0.911 |
| Paraffin oil | *** | | 0.1 | 0 | 0 | −19 | 39.3% | 202 | 0.880 |
| Example 15 | Succinic acid esterified first-fraction coconut fatty acid partial ester | 0.20 | 0.4 | 360 | 8.4 | −16 | 31.3% | 52.4 | 0.966 |
| Example 16 | Succinic acid | 0.40 | 0.3 | 393 | 8.6 | −37 | 24.9% | 116 | 0.992 |

TABLE 1-continued

| Example | Composition Substances | Mols S per mol G | Acid number | Sapon. number | Hydroxyl number | Turbidity point °C. | Evaporation loss 150° C./100 h | Viscosity (mm²/sec) | Density (20° C.) |
|---|---|---|---|---|---|---|---|---|---|
| Example 17 | Succinic acid esterified first-fraction coconut fatty acid partial ester | 0.54 | 0.25 | 418 | 9.2 | −51 | 20.3% | 222 | 1.008 |
| Example 18 | Succinic acid esterified first-fraction coconut fatty acid partial ester | 0.60 | 0.6 | 433 | 7.5 | Under −30 | 19.4% | 382 | 1.026 |
| Example 19 | Succinic acid esterified first-fraction coconut fatty acid partial ester | 0.80 | 0.24 | 478 | 13.6 | Under −70 | 14.1% | 4463 | 1.069 |

*First-fraction coconut fatty acid triglyceride
**Triglyceride based on predominantly unsaturated fatty acid and $C_{16}$ acid
***Isoparaffin
S = Succinic acid or succinic anhydride
G = Glycerin

COMPARATIVE EXAMPLE

The technical value of the new ester mixtures is apparent from a comparison with the known products listed below.

|  | Miglyol ®* | Peanut oil | Paraffin oil |
|---|---|---|---|
| Acid number | 0.1 | 0.11 | 0.1 |
| Hydroxyl number | 5.1 | 3.8 | 0 |
| Density at 20° C. | 0.950 | 0.911 | 0.880 |
| Turbidity point at 0° C. | 5 | 8 | −19 |
| Evaporation loss during 100 h at 150° C. | 42.9% | 6.8% | 39.3% |
| Viscosity at 20° C. | 29.8 | 93.6 | 202 |
| Viscosity at 37.8° C. (mm²/sec) | — | 41.7 | 42.4 |

*Miglyol 812 ® contains triglycerides of saturated $C_6$ acid (0.5 to 1 wt. %), $C_8$ acid (63 to 64 wt. %), $C_{10}$ acid (34 to 35 wt. %) and $C_{12}$ acid (0.5 to 2 wt. %)

The ester mixtures according the invention specifically may be used as a component of the oil base of creams for the pharmaceutical or cosmetical use, as more detailed may be seen from example 20. In cosmetical preparation the new products are effective as emolients for the skin. Furtheron the new products are very useful as lubricants in metal rolling processes, above all for the production of aluminium foils.

The new products of the invention are superior, compared with known substances, used for the same purposes, as shown from the advantages noted as 1 to 6 on the pages 7 and 8. The most valuable quality are very low turbidity points of −16° to −70° C. as comparable substances as liquid fatty oils have far higher turbidity points.

The stability against oxidation by atmospheric air is as high, that a storage of two years—until now—is possible without change, e.g. without occurance of any odor. No free fatty acids, no peroxides and no resinous substanced had been formed, while, for example, peanut oil forms 0.2 wt.% of free fatty acid and has a peroxide number of 5 to 10 after storage of 3 month.

The toxicologocal unocuousless may be seen from the fact, that products formed from fatty acid monoglycerides and succinic acid or other saturated aliphatic dicarboxilic acids are allowed in the United States as food additives.

What is claimed is:

1. Completely biodegradable, toxicologically innocuous, oxidation-resistant, flavorless and odorless, light-colored, homogeneous liquid ester mixtures with low turbidity points, low evaporation losses at elevated temperatures, and viscosities and densities adjustable as desired, comprising the products of esterification of 1 mol of glycerin with from 1.4 to 2.8 mols of a saturated aliphatic straight chained monocarboxylic acid having from 6 to 10 carbon atoms, or mixtures thereof, and from 0.1 to 0.8 mol of a saturated aliphatic dicarboxylic acid, or mixtures or anhydrides thereof, said ester mixtures having hydroxyl numbers ranging from 5 to 20 and an acid number of less than 5.

2. An ester mixture according to claim 1 wherein said product is the product of esterification of 1 mol glycerin and 1.6 to 2.6 mols of said monocarboxylic acid and 0.2 to 0.7 mols of said dicarboxylic acid.

3. A process for the preparation of completely biodegradable, oxidation-resistant, flavorless and odorless, light-colored, homogeneous liquid ester mixtures according to claim 1, wherein glycerin is esterified to hydroxyl-containing partial esters with an aliphatic straight chained monocarboxylic acid having from 6 to 10 carbon atoms, or mixtures thereof, in the ratio of 1 mol of glycerin to from 1.4 to 2.8 mols of aliphatic monocarboxylic acid at from 200° to 250° C., preferably under a vacuum, until an acid number of less than 50 is obtained, and simultaneously therewith or subsequent thereto the hydroxyl-containing partial esters are further esterified with from 0.1 to 0.8 mol of aliphatic dicarboxylic acids, or mixtures or anhydrides thereof, at from 200° to 250° C. until a hydroxyl number ranging from 5 to 20 and an acid number of less than 5 are obtained, the crude product then being decolorized and deodorized.

4. A process according to claim 3 wherein 1 mol glycerin is esterified with 1.8 to 2.6 mols of said monocarboxylic acid and 0.2 to 0.6 mols of said dicarboxylic acid.

5. An ester mixture according to claim 1 wherein said product has an acid number of less than 1.

6. A process according to claim 3 wherein the esterification with said dicarboxylic acid is under vacuum.

7. A process according to claim 3 wherein glycerin is esterified with a saturated aliphatic monocarboxylic acid having from 6 to 10 carbon atoms, or mixtures thereof, and simultaneously with aliphatic dicarboxylic acids, or mixtures or anhydrides thereof, at from 200° to 250° C. under a vacuum until a hydroxyl number ranging from 5 to 20 and an acid number of less than 5.

8. A process according to claim 7 wherein esterification with said dicarboxylic acid is at 220°–240° C.

9. A process according to claim 3 wherein the hydroxyl-containing glycerin partial esters are prepared in the absence of the aliphatic dicarboxylic acids, or mixtures or anhydrides thereof, and then esterified with aliphatic dicarboxylic acids.

10. A process according to claim 6 wherein the vacuum of the reaction mixture is gradually increased by about 5 to 50 mm Hg, and preferably 10 to 20 mm Hg, per hour in the presence of the aliphatic dicarboxylic acids, or mixtures or anhydrides thereof.

11. A completely biodegradable, toxicologically innocuous, oxidation-resistant, flavorless and ordorless, light-colored, homogeneous liquid ester mixture with low turbidity points, low evaporation losses at elevated temperatures, and viscosities and densities adjustable as desired, comprising the product of esterifying a mixture consisting essentially of 1 mol of glycerin with 1.4 to 2.8 mols of a saturated aliphatic straight chained monocarboxylic acid having from 6 to 10 carbon atoms, or mixtures thereof, and from 0.1 to 0.6 mol of a saturated aliphatic dicarboxylic acid, or mixtures or anhydrides thereof, said ester mixtures having hydroxyl numbers ranging from 5 to 20 and an acid number of less than 5 prepared by the process of claim 3.

* * * * *

UNITED STATES PATENT AND TRADEMARK OFFICE
CERTIFICATE OF CORRECTION

PATENT NO. : 4,366,100

DATED : December 28, 1982

INVENTOR(S) : Sasanka S. Naskar et al

It is certified that error appears in the above—identified patent and that said Letters Patent is hereby corrected as shown below:

Col. 4, line 64      Delete "diphlegmator" and insert --dephlegmator--

Col. 11, line 41      After "Turbidity point at" delete "0°C" and insert --20°C--

Signed and Sealed this

Seventh Day of June 1983

[SEAL]

*Attest:*

DONALD J. QUIGG

*Attesting Officer*      *Acting Commissioner of Patents and Trademarks*